United States Patent
Yoda et al.

(10) Patent No.: US 6,256,591 B1
(45) Date of Patent: Jul. 3, 2001

(54) METHOD OF FORMING ENERGY DISTRIBUTION

(75) Inventors: Kiyoshi Yoda; Hidenobu Sakamoto; Yoshifuru Saitou, all of Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/091,158

(22) PCT Filed: Jul. 15, 1997

(86) PCT No.: PCT/JP97/02459

§ 371 Date: Jun. 9, 1998

§ 102(e) Date: Jun. 9, 1998

(87) PCT Pub. No.: WO98/23330

PCT Pub. Date: Jun. 4, 1998

(30) Foreign Application Priority Data

Nov. 26, 1996 (JP) .................................................. 8-315279

(51) Int. Cl.[7] .................................................. G06F 17/00
(52) U.S. Cl. .......................... 702/57; 702/65; 250/492.3; 250/363.04
(58) Field of Search .................................. 702/57, 40, 65, 702/66, 60–62, 106, 107, 115, 124, 126, 134, 156, 159, 172, 183, 189, 193, FOR 103, FOR 104, FOR 106, FOR 110, FOR 123, FOR 125, FOR 131, FOR 134, FOR 135, FOR 148, FOR 145, FOR 149, FOR 170, FOR 171; 700/286, 245; 324/312, 96, 76.14; 378/205, 4, 5, 9, 21, 49, 70, 901; 250/492.3, 491.1, 493.1, 494.1, 505.1, 492.1, 492.22, 366–368, 362, 363.01, 363.08, 363.03, 363.05

(56) References Cited

U.S. PATENT DOCUMENTS

| | | | |
|---|---|---|---|
| 5,039,867 | 8/1991 | Nishihara et al. | 250/492.3 |
| 5,635,714 | * 6/1997 | Nablo et al. | 250/492.3 |
| 5,650,935 | * 7/1997 | Nishino et al. | 702/57 |
| 5,780,856 | * 7/1998 | Oka et al. | 250/367 |

FOREIGN PATENT DOCUMENTS 7-275382  10/1995 (JP) .
8-280824  10/1996 (JP) .

OTHER PUBLICATIONS

"Optimal Design of Exciting Coils" by Katoh et al, Mar. 8, 1994, pp. 1–4, Partial for Solution of Document College of Engr., Hosei University.

"Broad Beam Three Dimensional Irradition for Proton Radiotherapy" by Kanai et al, Am.Ass. of Phys. Med., Technical Notes, pp. 344–346, May/Jun. 1983.

"Dose Calculations in Proton Beams: Range Straggling corrections and Energy Scaling" by Russell et al., Phys. Med. Bio. 40 (1995), pp. 1031–1043. (No month).

"The Influence of Thick Inhomogeneities on Charged Particle Beams" by Goitein et al, Radiation Research 74, 217–230 (1978). (No month).

"Three Dimensional Beam Scanning for Proton Therapy" by Kanai et al, Nuclear Iinstruments and Methods, 214 (1983) pp. 491–496. (No month).

* cited by examiner

Primary Examiner—Hal Wachsman
(74) Attorney, Agent, or Firm—Sughrue, Mion, Zinn, Macpeak & Seas, PLLC

(57) ABSTRACT

The ratio a between an energy distribution vector $U_P$ is calculated by using a density distribution P, and a desired energy distribution vector V to obtain an energy source density distribution P/a. Thus, the intensity of an energy distribution can be varied, and the irradiation of unnecessary portions of the human body can be avoided when an tumor in the human body is irradiated with an energy distribution.

10 Claims, 19 Drawing Sheets

ELECTRIC FIELD SETTING POSITION

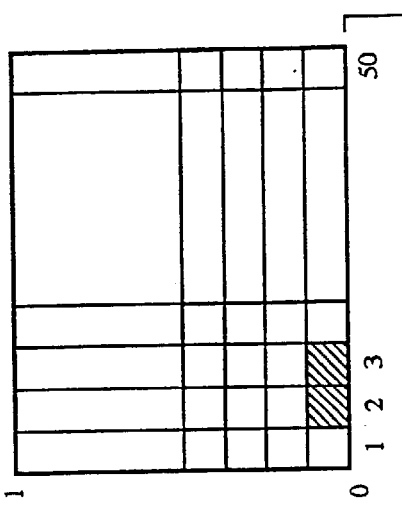
FIG.5c
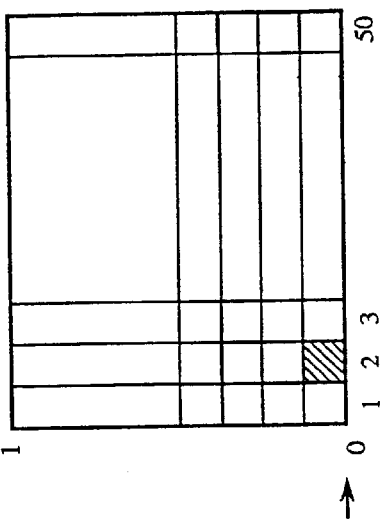
FIG.5b
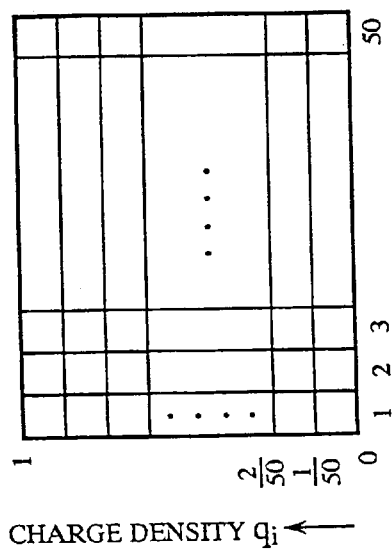
FIG.5a
CHARGED POSITION $x_i$ →
CHARGE DENSITY $q_i$ ←
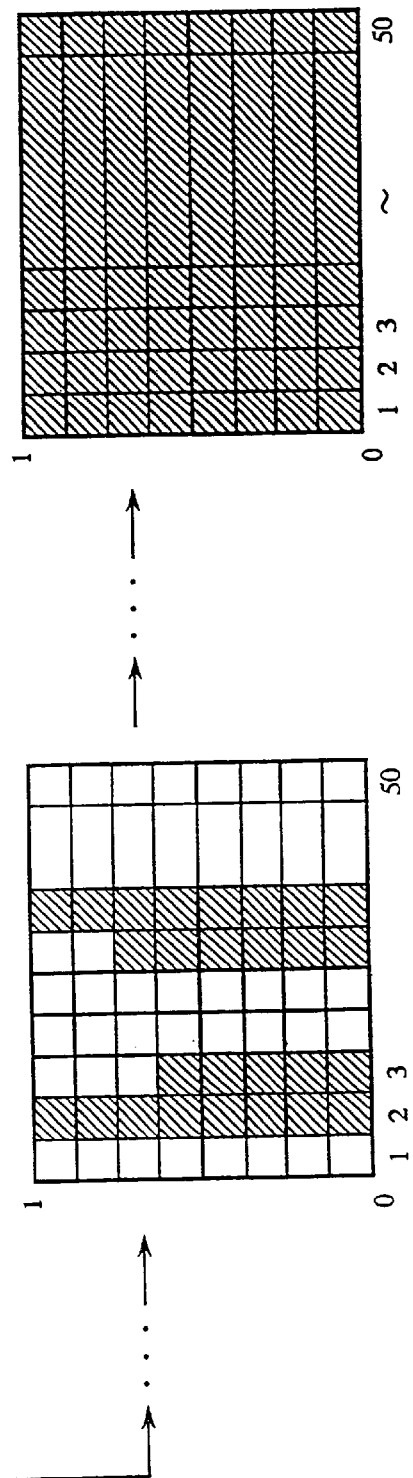
FIG.5e
FIG.5d

POSITION X WITH RESPECT TO
A LATERAL DIRECTION

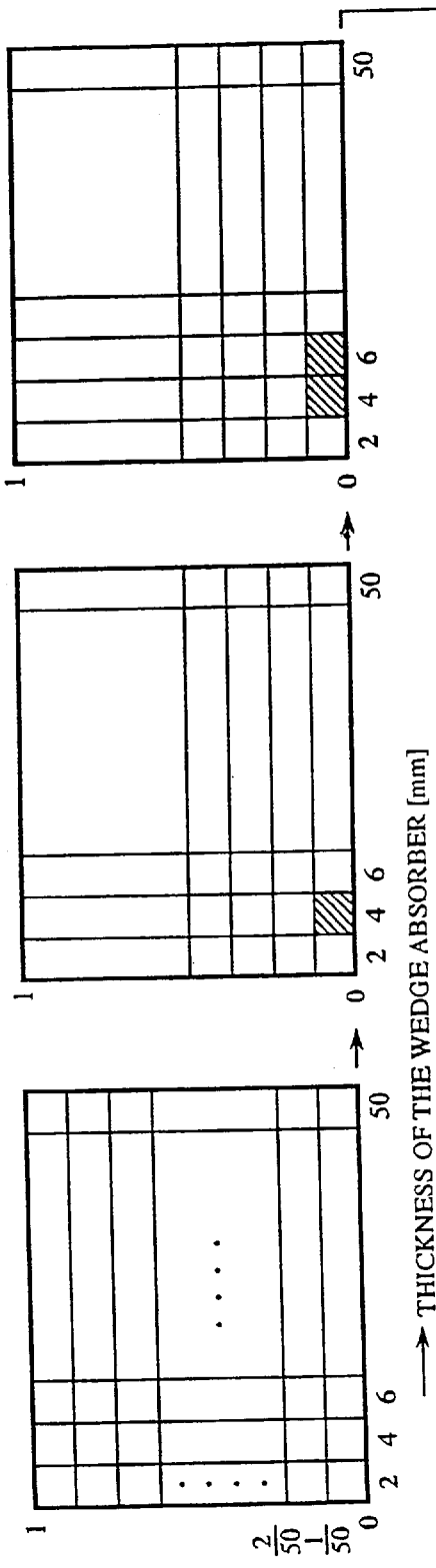
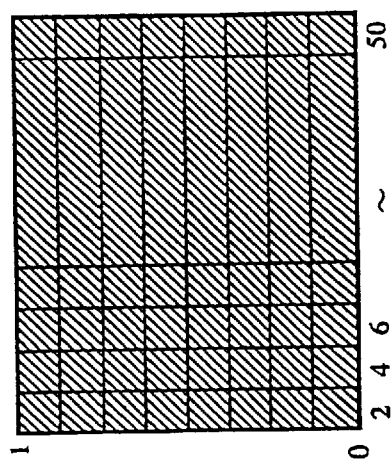
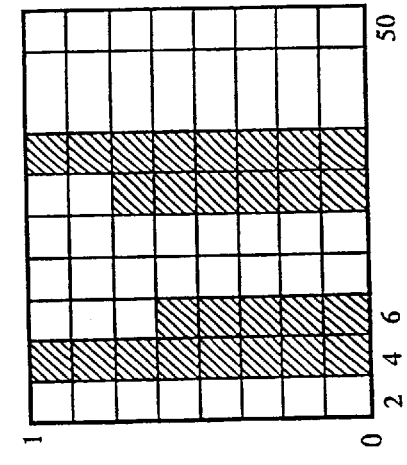
FIG.20a FIG.20b FIG.20c FIG.20d FIG.20e
→ THICKNESS OF THE WEDGE ABSORBER [mm]
← PROTON BEAM RADIATION DOSE $q_i$

●●● DESIRED INTERNAL DOSE
DISTRIBUTION V

METHOD OF FORMING ENERGY DISTRIBUTION

TECHNICAL FIELD

The present invention relates to a method of forming an energy distribution by determining an energy source to be given to a system so that an energy distribution created in the system coincides with a desired distribution.

BACKGROUND ART

A conventional energy distribution forming method disclosed in, for example, "Denki Gakkai Magunetikkusu Kenkyukai Shiryo", MAG-94-26, pp. 63–69 (1994) is called a sampled pattern matching method (hereinafter abbreviated to "SPM method").

The SPM method is employed for determining a distribution pattern of an energy source forming a desired field when a distribution (electric field distribution, magnetic field distribution, radiation intensity distribution, temperature distribution or the like) in the desired field is given. To put it concretely, the SPM method arranges lattice points in a space and makes sequential search to find a point which makes an energy source assumed to be at that point form a pattern close to the distribution of the desired field. Search is terminated upon the increase of the coincidence degree of the pattern created by the energy source with the distribution of the desired field to a maximum.

The pattern coincidence degree is evaluated by an angle $\theta$ made between a measured distribution pattern vector $V$ and a calculated distribution pattern vector $U$. Concretely, pattern coincidence degree is defined by the following equality (1):

$$\gamma = \cos\theta = U \cdot V / (|U||V|) \qquad (1)$$

where $U \cdot V$ is inner product, and $|U|$ and $|V|$ indicate the respective magnitudes of the vectors $U$ and $V$.

FIG. 1(a) shows a desired magnetic field distribution 101, and FIG. 1(b) shows an arc-shaped coil 102 having the shape of a circular arc for creating a magnetic field distribution close to the desired magnetic field distribution estimated by the SPM method. FIG. 1(c) shows a magnetic field distribution 103 formed by the arc-shaped coil 102 in FIG. 1(b). The size of the circle is illustrated to be proportional to magnetic field intensity. The magnetic field distribution 103 realizes approximately the same as the magnetic field pattern shown in FIG. 1(a), which proves the effectiveness of the SPM method. It should be noted that constant current must be supplied to the coil because the foregoing method only distributes unit current sources and is unable to vary the amplitude of the current in principle.

Since the conventional method of forming an energy distribution is thus constructed, the position of an energy source having a fixed intensity can be determined, but there remains a problem the intensity of the energy source is invariable.

The present invention has been made to solve the foregoing problem and it is therefore an object of the present invention to provide an energy distribution forming method capable of varying the intensity of energy source distribution.

DISCLOSURE OF THE INVENTION

The present invention comprises a first step of determining a minimum value $q_{min}$ and a maximum value $q_{max}$ for energy source density, a second step of setting the minimum energy source density $q_{min}$ at m energy source density setting positions $x_i$ ($i=1, \ldots, m$), a third step of increasing by a predetermined value $\Delta q$ an energy source densities $q_i$ at the positions $x_i$ ($i=1, \ldots, m$) excluding the energy source density setting positions $x_i$ where $q_i + \Delta q > q_{max}$, thereby calculating energy distribution vectors $U_i$, a fourth step of calculating pattern coincidence degree $\gamma_i$ from the calculated energy distribution vectors $U_i$ and a desired energy distribution vector $V$, a fifth step of changing the energy source density at the position $x_i$ which gives the largest pattern coincidence degree to $q_i + \Delta q$, a sixth step of repeating the third step to the fifth step until the energy source densities at all the positions $x_i$ reach the maximum energy source density $q_{max}$ and searching out an energy source density distribution P which gives the largest pattern coincidence degree, and a seventh step of calculating the ratio a between an energy distribution vector $U_P$ calculated by using the density distribution P searched out in the sixth step, and the desired energy distribution vector $V$ to obtain an energy source density distribution P/a. Thus, input energy which gives a desired energy distribution can be efficiently obtained.

The present invention comprises a first step of determining a minimum value $q_{min}$ and a maximum value $q_{max}$ for energy source density, a second step of setting the maximum energy source density $q_{max}$ at m energy source density setting positions $x_i$ ($i=1, \ldots, m$), a third step of decreasing by a predetermined value $\Delta q$ an energy source densities $q_i$ at the positions $x_i$ ($i=1, \ldots, m$) excluding the positions $x_i$ where $q_i - \Delta q < q_{min}$ and calculating energy distribution vectors $U_i$, a fourth step of calculating pattern coincidence degrees $\gamma_i$ from the calculated energy distribution vectors $U_i$ and a desired energy distribution vector $V$, a fifth step of changing the energy source density at the position $x_i$ which gives the largest pattern coincidence degree to $q_i - \Delta q$, a sixth step of repeating the third step to the fifth step until the energy source densities at all the positions $x_i$ reach the minimum energy source density $q_{min}$ and searching out an energy source density distribution P which gives the largest pattern coincidence degree and a seventh step of calculating the ratio a between an energy distribution vector $U_P$ calculated by using the density distribution P searched out in the sixth step, and the desired energy distribution vector $V$ to obtain an energy source density distribution P/a. Thus, input energy which gives a desired energy distribution can be efficiently obtained.

The present invention selects one of an electric charge density distribution, a particle beam intensity distribution, a current density distribution, a voltage source distribution, an electromagnetic field source distribution, a radiation source distribution, a heat source distribution, a light source distribution, a load distribution, a sound source distribution and a magnetization distribution as an energy source distribution. Thus, an energy source can be easily selected.

The present invention selects one of an electric field distribution, a particle dose distribution, a potential distribution, an electromagnetic field distribution, a stress distribution, a displacement distribution, a temperature distribution, a flow velocity distribution, a sound pressure distribution and a radiation intensity distribution as energy distribution. Thus, energy distribution can be easily selected.

The present invention uses the cosines of the angles between calculated energy distribution vectors $U_i$ and the desired energy distribution vector $V$ as pattern coincidence degrees. Therefore, input energy which gives the desired energy distribution can be efficiently obtained.

The present invention uses the sines of the angles between calculated energy distribution vector $U_i$ and the desired energy distribution vector V as pattern coincidence degrees. Therefore, input energy which gives the desired energy distribution can be efficiently obtained.

The present invention selects a proton dose distribution as a particle dose distribution, and a proton beam intensity distribution as a particle beam intensity distribution. Therefore, an energy intensity distribution having a sharp rising characteristic and a sharp falling characteristic can be easily obtained.

The present invention selects a particle dose distribution as an energy source distribution, and selects an internal particle dose distribution as an energy distribution. Therefore, a desired internal radiation dose distribution can be set. For example, the interior of an tumor can be irradiated with radiation in a uniform dose distribution limiting radiation dose in normal tissues around the tumor to a minimum, so that the tumor can be effectively treated and the side effects of radiation can be reduced.

The present invention selects a proton beam as a particle beam. Thus, a desired internal radiation dose distribution can be set for proton treatment. For example, the interior of an tumor can be irradiated with radiation in a uniform dose distribution, limiting radiation dose in normal tissues around the tumor to a minimum, so that the tumor can be effectively treated and the side effects of radiation can be reduced.

BRIEF DESCRIPTION OF THE DRAWINGS

FIGS. 5a–5e is a diagrammatic view of assistance in explaining a process of determining a charge distribution;

FIGS. 20a–20e are a diagrammatic view of assistance in explaining a process of determining proton dose for the thickness of a wedge absorber;

BEST MODE FOR CARRYING OUT THE INVENTION

Best mode for carrying out the present invention will be described in detail hereinafter with reference to the accompanying drawings.

First Embodiment

Figure 1C:
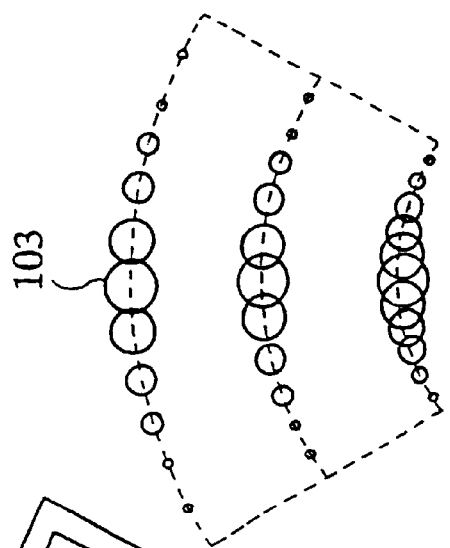
FIGS. 1a–1c are a diagrammatic view of assistance in explaining a conventional SPM method.
Figure 1B:
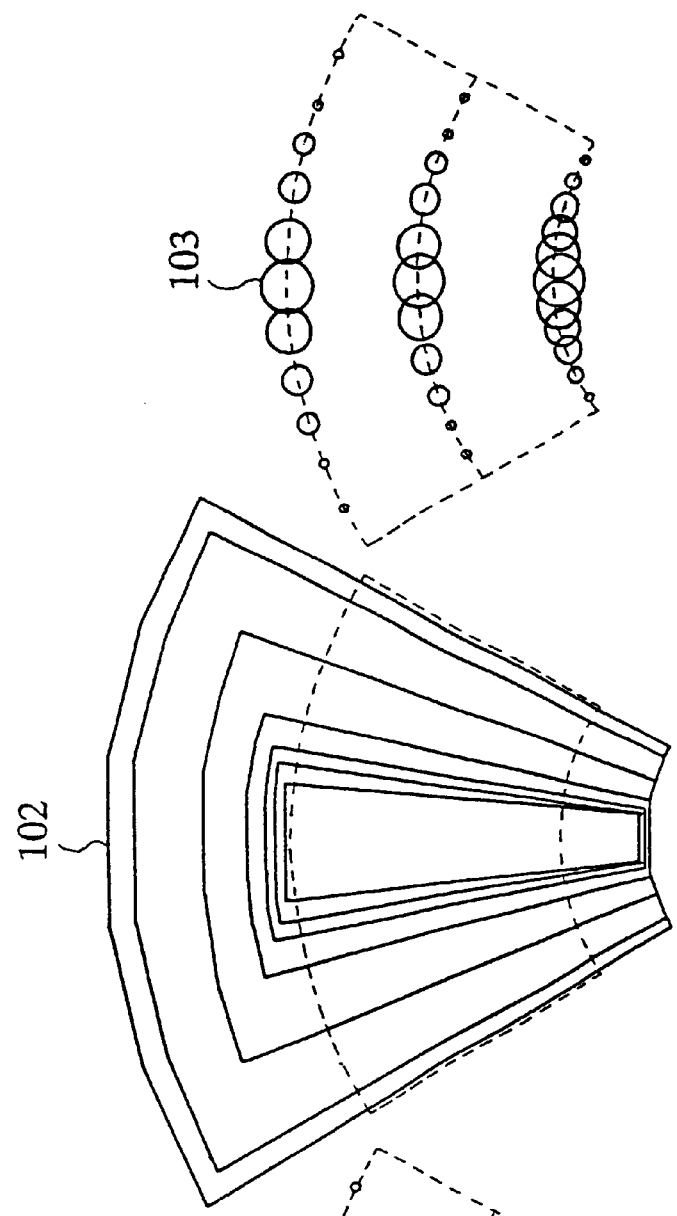
Figure 1A:
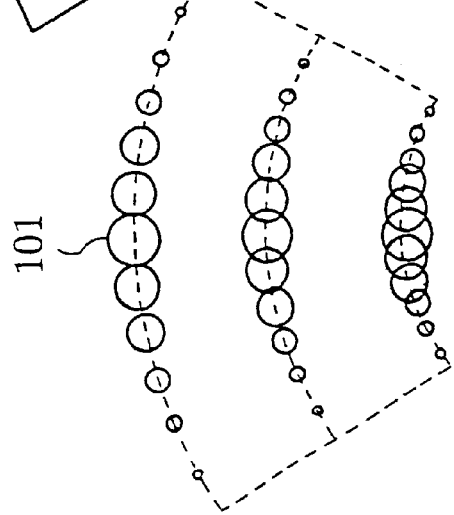
Figure 2:
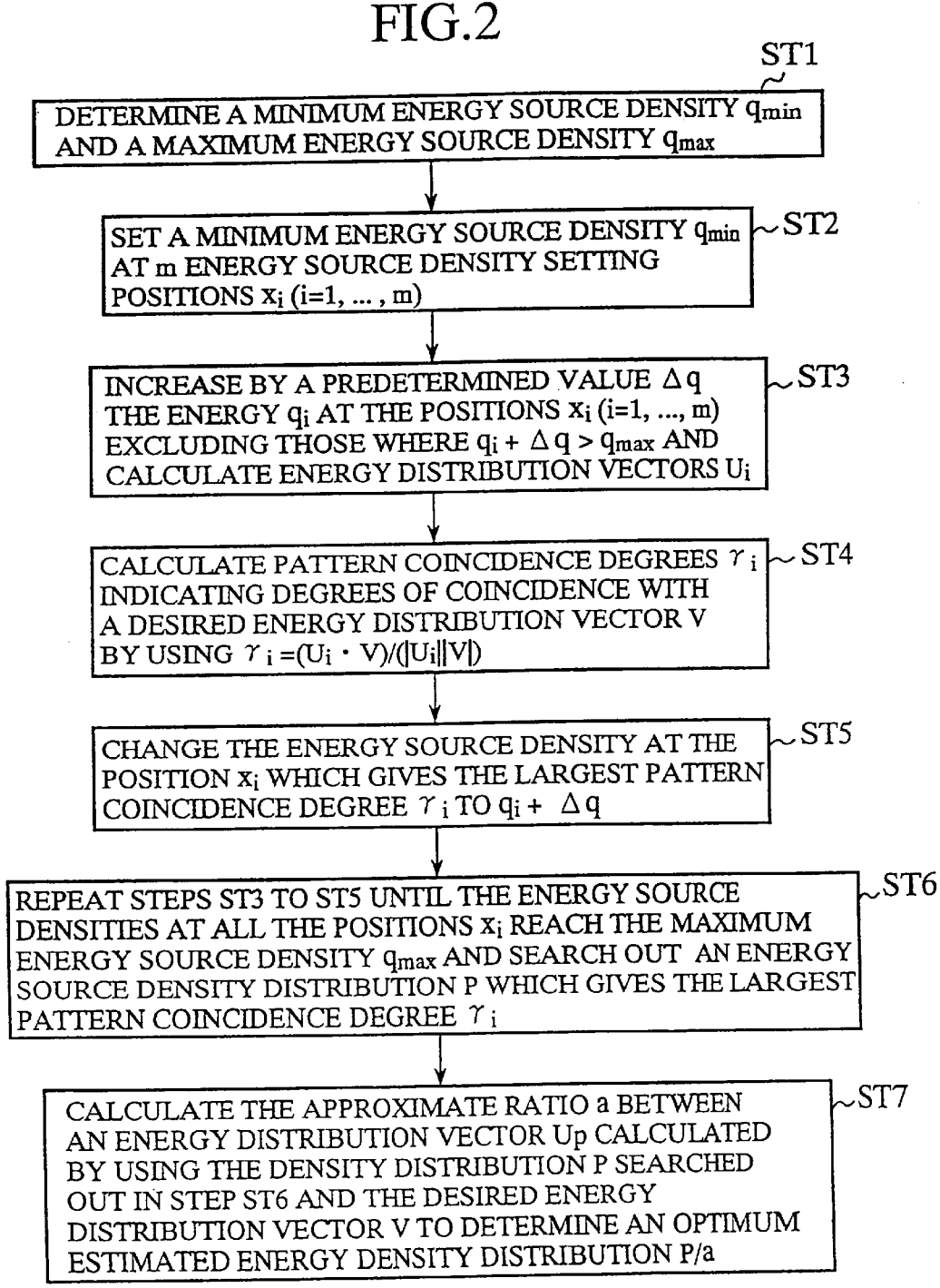
FIG. 2 is a flow chart of an energy distribution forming method in a first embodiment according to the present invention.

FIG. 2 is a flow chart of an energy distribution forming method in a first embodiment according to the present invention. Referring to FIG. 1, a minimum energy source density $q_{min}$ and a maximum energy source density $q_{max}$ are determined in step ST1. The minimum energy source density $q_{min}$ is set at m energy source density setting positions (hereinafter, referred to simply as "positions") $x_i$ (i=1, ..., m) in step ST2. The energy $q_i$ at the positions $x_i$ (i=1, ..., m) is increased by a predetermined value $\Delta q$ and energy distribution vectors $U_i$ are calculated, excluding the positions $x_i$ where $q_i+\Delta q>q_{max}$ in step ST3.

The cosines of the angles between the calculated energy distribution vectors $U_i$ and a desired energy distribution vector V as pattern coincidence degrees $\gamma_i$ are calculated in step ST4. The energy source density at the position $x_i$ which gives the largest pattern coincidence degree $\gamma_i$ is changed to $q_i+\Delta q$ in step ST5. Steps ST3 to ST5 are repeated in step ST6 until the energy source densities at all the positions $x_i$ reach the maximum energy source density $q_{max}$ to search out an energy source density distribution P which gives the largest pattern coincidence degree $\gamma_i$. The approximate ratio a between an energy distribution vector $U_P$ calculated by using the density distribution P searched out in step ST6 and the desired energy distribution vector V is calculated to determine an optimum estimated energy density distribution P/a in step ST7.

The operation will be described hereinafter with reference to FIGS. 3 to 6.

Figure 3:
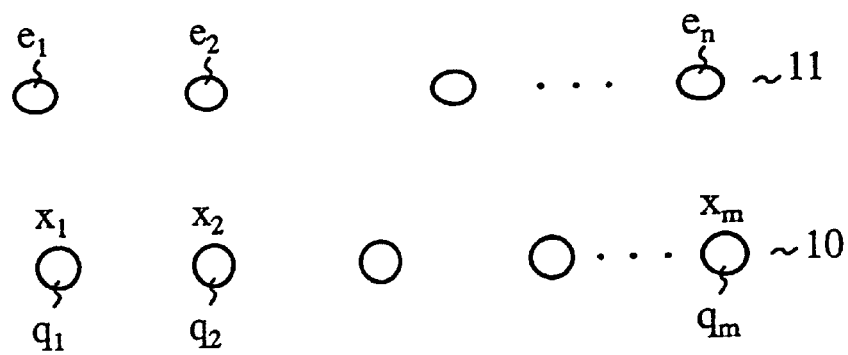
FIG. 3 is a diagram of assistance in explaining the relation between m charge densities and n electric field setting points in a space.
Figure 4:
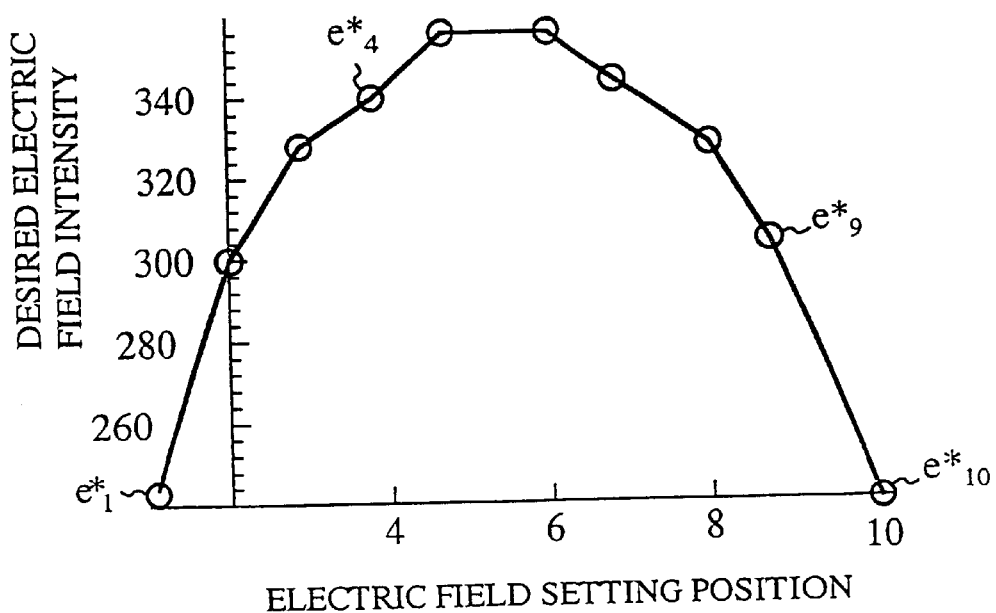
FIG. 4 is a graph showing the distribution of desired electric field intensity as a function of electric field setting position.

Shown in FIG. 3 is a linear space in which charges $q_i$ to $q_m$ are distributed. Suppose that electric field intensities $e_i$ to $e_m$ exist at n electric field setting points which determines a charge distribution which gives a desired electric field intensity distribution on an observation point 11 above the space 10 in which the m charges $q_i$ to $q_m$ exist. It should be noted that in FIG. 3, indicated at $x_i$ to $x_m$ are m energy source density setting positions (hereinafter referred to simply as "positions"). The number m of charges is 50.

In step ST1, a minimum charge $q_{min}$ and a maximum charge $q_m$ among the charges $q_i$ to $q_m$ are determined. For example, the minimum charge $q_{min}=0$ if a desired electric field distribution is formed only by positive charges. Although the maximum charge $q_{max}$ may be any optional positive charge, $q_{max}=1$ herein for simplicity. The absolute value of amplitude can be obtained by determining a relative amplitude distribution, and multiplying the relative amplitude distribution by a proportional constant. If there is no any restriction on the signs of the charges $q_i$ to $q_m$, $q_{min}=-1$ and $q_{max}=1$ may be used. If the electric field distribution is desired to be formed by only negative charges, it is possible that $q_{max}=0$, and $q_{min}$ may be an optional negative value. In this case, $q_{max}=-1$ for simplicity.

In step ST2, m positions are defined at equal intervals in the space 10 in which the charges $q_i$ to $q_m$ exist. Suppose that charges $q_i$ to $q_m$ at the positions are equal to $q_{min}$. Then, in the first embodiment, only positive charges are used to form the electric field distribution. Accordingly, it is supposed that the charges at the respective positions $x_i$ are zero; that is, $q_{min}=0$ and $q_{max}=1$.

In step ST3, a minimum unit charge $\Delta q$ is added to the charges at the respective positions $x_i$ and field intensity vectors are calculated. Suppose that charges $q_i$ (i=1, ..., 50) exist in the space 10, field intensities $e_j$ (j=1, ..., 10) at the observation points 11 are calculated theoretically, and a system matrix A is defined. The j rows and i columns of component $A_{ji}$ of the system matrix are expressed by the following equality (2):

$$A_{ji}=1/(4\pi\epsilon r_{ji}^2) \qquad (2)$$

where $r_{ji}$ is the distance between the position $x_i$ which gives a charge $q_i$ and the position which gives an electric field intensity $e_j$, that is, the distance from the space 10 to the observation point 11. In this state, the relation between an electric field intensity distribution vector $U=(e_1, e_2, ..., e_{10})^T$ and a charge distribution vector $Q=(q_1, q_2, ..., q_{50})^T$ is expressed by the following equality (3): where T is a transposition of a vector $$U=AQ \qquad (3)$$

where U is the vector of ten rows, A is a 10-row 50-column matrix and Q is the vector of fifty rows.

Note that initial setting is $Q=(0, 0, ..., 0)^T$ in step ST2 as shown in FIG. 5(a). In step ST3, fifty possible choices: $Q_i=(\Delta q, 0, 0, ..., 0)^T$, $Q_2=(0, \Delta q, 0, ..., 0)^T$, $Q_3=(0, 0, \Delta q, 0, ..., 0)^T$, ... and $Q_{50}=(0, ..., 0, \Delta q)^T$ are prepared, and electric field intensity distribution vectors $U_1$ to $U_{50}$ are calculated for charge distributions $Q_1$ to $Q_{50}$ on the basis of Expression (3) by using Expression (4).

$$U_i=AQ_i (i=1, ..., 50) \qquad (4)$$

where $\Delta q$ is a value obtained by diving ($\Delta q_{max}-q_{min}$) by an appropriate positive integer. In this case, $\Delta q=1/50$, which is equivalent to determination made by quantizing intensity information in fifty steps. Since the conventional SPM method does not take this into consideration, intensity cannot be varied.

In step ST4, a desired electric field intensity distribution vector is defined by: $V=(e_1, e_2, ..., e_{10})^T$, and the angles $\theta_i$ (i=1, ..., 50) between the desired electric field intensity distribution vector V and the distribution pattern vectors $U_i$ calculated in step ST3 (i=1, ..., 50) are evaluated. Pattern coincidence degrees $\gamma_i$ are calculated by using:

$$\gamma_i=\cos \theta_i=U_i\cdot V/(|U_i||V|) \qquad (5)$$

where $U_i\cdot V$ is the inner product of vectors, and $|U_i|$ and $|V|$ indicate the magnitudes of the vectors $U_i$ and V, respectively.

In step ST5, the energy source density at the position $x_i$ which gives the largest pattern coincidence degree $\gamma_i$ is changed to $\Delta q$. For example, if i=2, $Q_2=(0, \Delta q, 0, ..., 0)^T$ is selected a new charge distribution vector as shown in FIG. 5(b).

In step ST6, fifty candidate charge vectors $Q_1=(\Delta q, \Delta q, 0, ..., 0)$, $Q_2=(\Delta q, 2\Delta q, 0, ..., 0)^T$, $Q_3=(0, \Delta q, \Delta q, 0 ..., 0)^T$, ..., $Q_{50}=(0, \Delta q, 0, ... 0, \Delta q)^T$ are newly produced by increasing one of the charges of the new charge distribution vectors determined in step ST5. Pattern coincidence degrees $\gamma_i$ are determined by calculation in steps ST3 and ST4. The charge at the position $x_i$ which gives the largest pattern coincidence degree $\gamma_i$ is increased by $\Delta q$.

Subsequently, if i=3, the new charge distribution vector: $Q_3=(0, \Delta q, \Delta q, 0, ..., 0)^T$ is selected as shown in FIG. 5(c). This procedure is repeated until all the charges coincides with the maximum value of 1. If the charge at a position $x_i$ increases to the maximum set value of 1 during the execution of the procedure, further increase is against the assumptions of the model. Therefore, the charge of that position $x_i$ is fixed and a search out process is continued for only the charge densities at the rest of the positions as shown in FIGS. 5(d) and 5(e). A charge distribution P which gives the largest pattern coincidence degree is searched out during this calculation process.

In step ST7, the ratio a between an energy distribution vector UP calculated by using the density distribution P searched out in step ST6, and the desired energy distribution vector V to obtain P/a as a charge distribution. Since the calculation is based on an assumption that the maximum charge is 1, this is a necessary means for determining the absolute value of a charge distribution.

Figure 6:
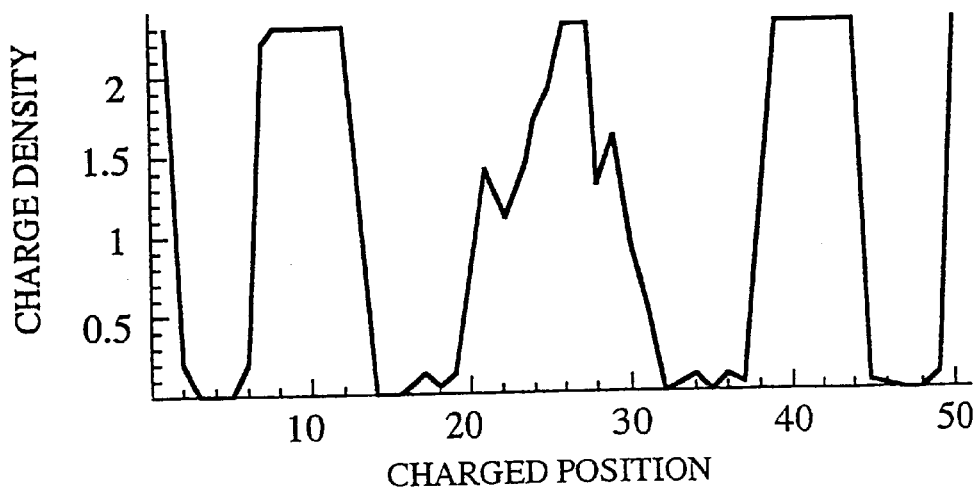
FIG. 6 is a graph of assistance in explaining the energy distribution forming method in the first embodiment, showing a charge density distribution with respect to charged position.
Figure 7:
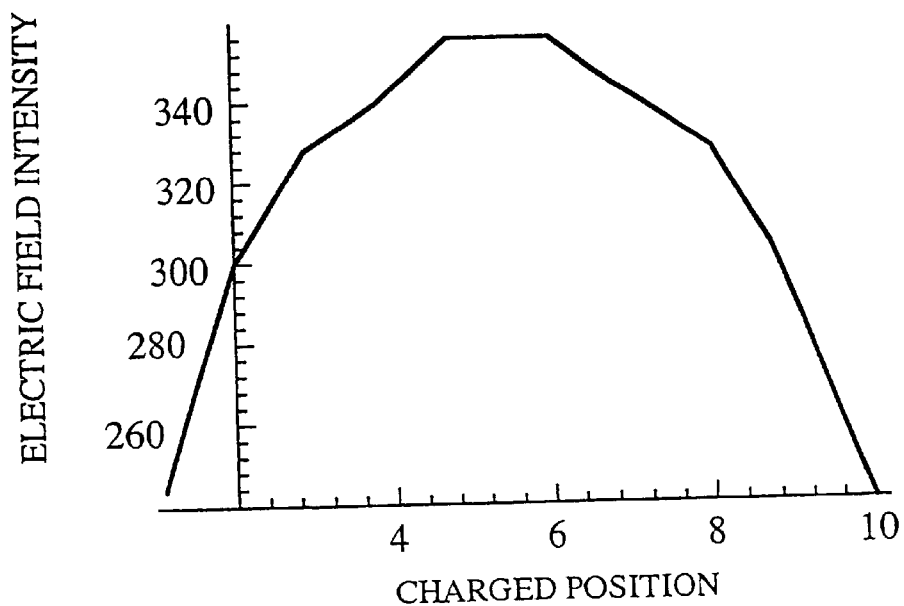
FIG. 7 is a graph of assistance in explaining the energy distribution forming method in the first embodiment, showing an electric field intensity distribution with respect to charged position.

FIG. 6 is a graph showing the thus determined charge density distribution, i.e., charge densities at the charged positions. FIG. 7 is a graph showing the electric field intensity distribution, i.e., electric field intensities at the charged positions. The electric field intensity distribution coincides satisfactorily with the desired electric field intensity distribution for the electric field setting position shown in FIG. 4; that is, a desired electric field intensity distribution is formed.

The foregoing series of steps are only example of the method of the present invention and may be substituted by a mathematically equivalent operations for the same effect. For example, the angle between the energy distribution vector $U_i$ and the desired energy distribution vector V calculated in step ST4 may be used as an evaluation function, and an energy source density distribution P which makes the angle a minimum may be searched out in step ST6. It is also possible to use the sine of the angle between the desired energy distribution vector V and the energy distribution vector $U_i$ calculated in step ST4 may be used as an evaluation function, and to search out an energy source density distribution P which makes the evaluation function a minimum in sixth step ST6.

Second Embodiment

Figure 8:
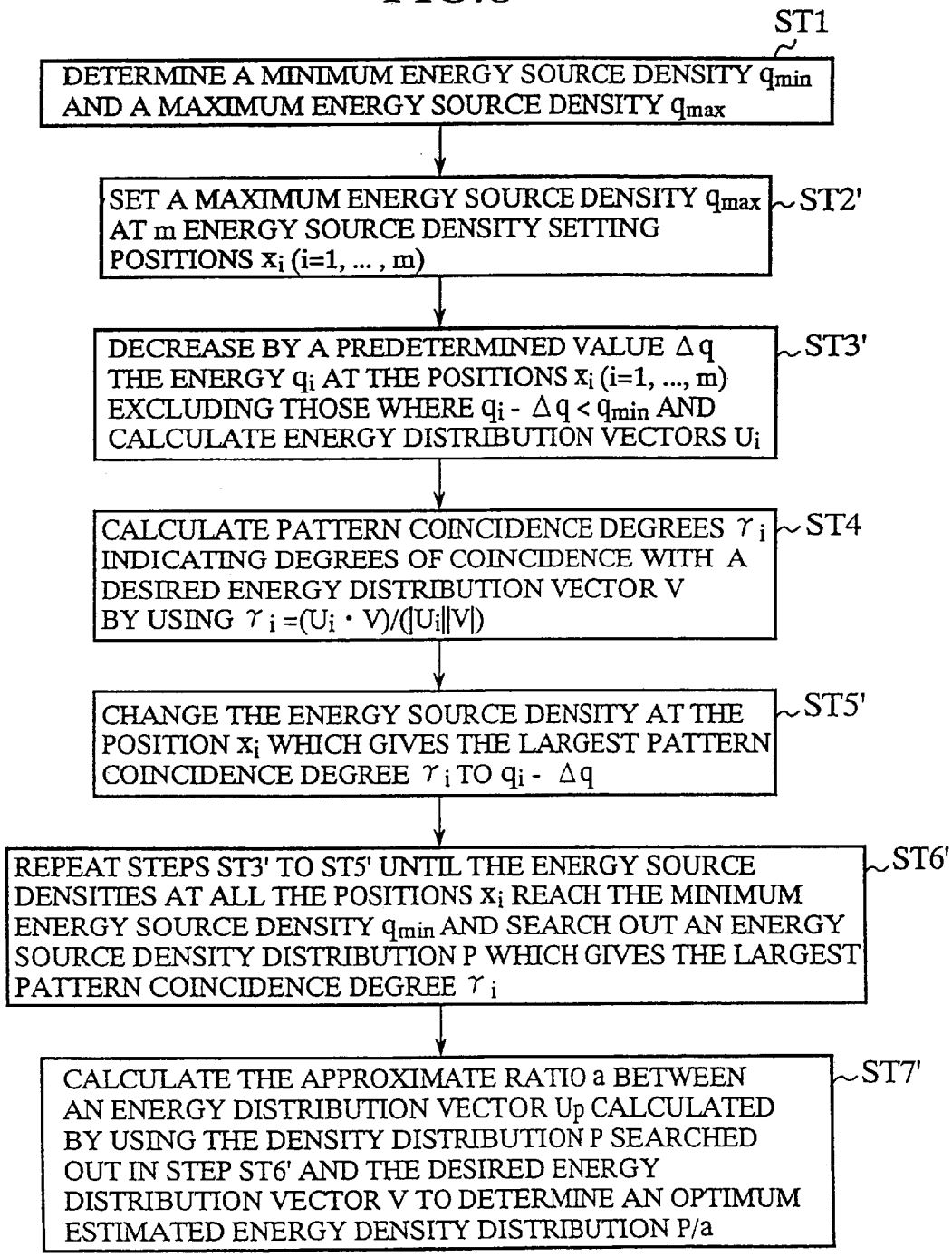
FIG. 8 is a flow chart of an energy distribution forming method in a second embodiment according to the present invention.

FIG. 8 is a flow chart of an energy distribution forming method in a second embodiment according to the present invention. Referring to FIG. 8, a minimum energy source density $q_{min}$ and a maximum energy source density $q_{max}$ are determined in step ST1. The minimum energy source density $q_{min}$ is set at m energy source density setting positions $x_i$ (i=1, ..., m) in step ST2'. The energy $q_i$ at the positions $x_i$ (i=1, ..., m) is decreased by a predetermined value $\Delta q$ and energy distribution vectors $U_i$ are calculated, excluding those for $q_i - \Delta q < q_{min}$ in step ST3'.

In step ST4, the cosines of the angles between the calculated energy distribution vectors $U_i$ and a desired energy distribution vector V are calculated to be as pattern coincidence degrees $\gamma_i$. The energy source density at the position $x_i$ which gives the largest pattern coincidence degree $\gamma_i$ is changed to $(q_i - \Delta q)$ in step ST5'. Steps ST3' to ST5' are repeated in step ST6' until the energy source densities at all the positions $x_i$ reach the minimum energy source density $q_{min}$ to search out an energy source density distribution P which gives a maximum value of pattern coincidence degree $\gamma_i$. The approximate ratio a between an energy distribution vector $U_P$ calculated by using the density distribution P searched out in step ST6' and the desired energy distribution vector V to determine an optimum estimated energy density distribution P/a in step ST7'.

The functions of the second embodiment differ from those shown in FIG. 2 only in that a search procedure employed in the second embodiment sets a maximum charge at all the positions, and then the maximum charge is decreased sequentially by $\Delta q$ in step ST3'.

Figure 9:
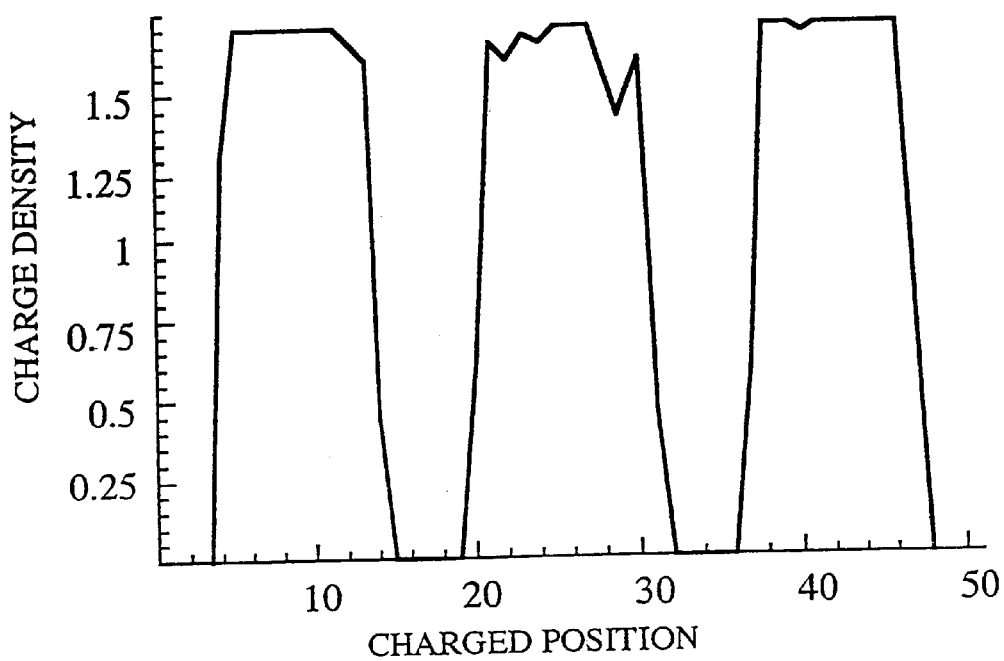
FIG. 9 is a graph of assistance in explaining the energy distribution forming method in the second embodiment, showing a charge density distribution with respect to charged position.
Figure 10:
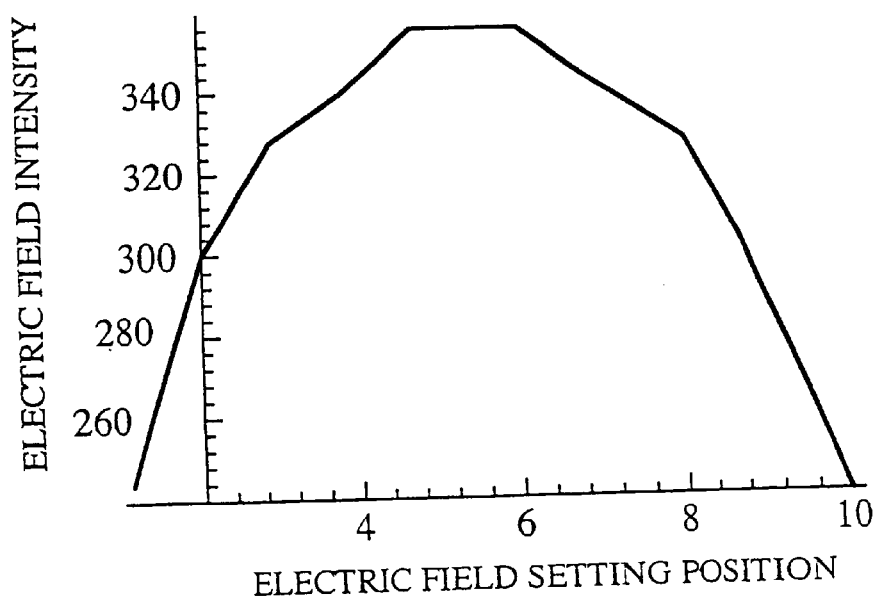
FIG. 10 is a graph of assistance in explaining the energy distribution forming method in the first embodiment, showing an electric field intensity distribution with respect to charged position.

Therefore, the first embodiment expressed by the procedure shown in FIG. 2 may be called an additive method, and the second embodiment expressed by the procedure shown in FIG. 8 may be called a subtractive method. FIG. 9 is a graph showing the thus determined charge density distribution, i.e., charge densities at the charged positions. FIG. 10 is a graph showing the electric field intensity distribution, i.e., electric field intensities at the charged positions. The electric field intensity distribution coincides satisfactorily with the desired electric field intensity distribution for the electric field setting position shown in FIG. 4; that is, a desired electric field intensity distribution is formed.

Third Embodiment

Figure 11:
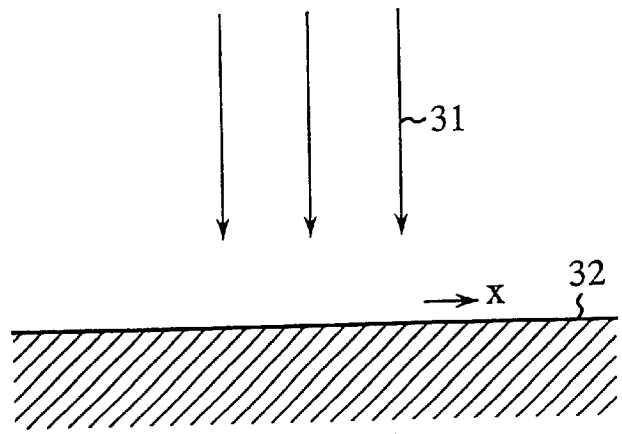
FIG. 11 is a diagrammatic view of assistance in explaining an energy distribution forming method in a third embodiment according to the present invention.

FIG. 11 is a view of assistance in explaining an energy distribution forming method in a third embodiment according to the present invention. The third embodiment, for example, determines an irradiation intensity distribution (energy source distribution) in a pencil beam (proton beam) 31 so that a desired radiation dose distribution (energy distribution) is formed in the human body 32 when irradiating the human body 32 with the pencil beam 31.

Figure 12:
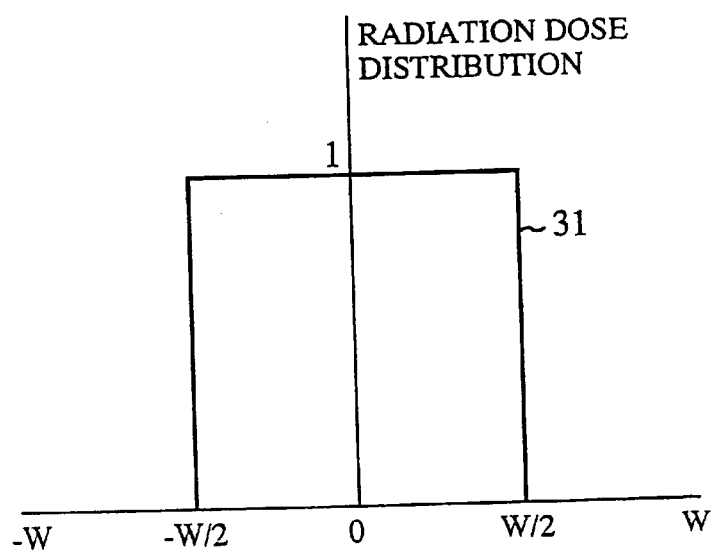
FIG. 12 is a diagram showing a radiation dose distribution with respect to position with respect to a lateral direction.

FIG. 12 shows a desired radiation dose distribution, namely, a radiation dose distribution with respect to a direction perpendicular to the pencil beam 31 (lateral direction). The pencil beam 31 is formed so that radiation dose distribution is uniform in a range of a width W and radiation dose outside the range is zero. Suppose that the pencil beam 31 has an incident energy E, and the lateral distribution (distribution in the X-direction) in the pencil beam 31 is a Gaussian distribution. If the pencil beam 31 is moved laterally for scanning, a dose distribution D(x, 0) on the surface of the human body can be expressed by:

$$D(x, 0) = \int_{-\infty}^{\infty} I(x') \frac{e^{-\frac{(x-x')^2}{\sigma^1}}}{\pi\sigma^2} dx' S(E, 0) \tag{6}$$

where I(x) is the intensity of the pencil beam at coordinates x, $\sigma$ is 1/e scattering length on the surface of the human body 32 as a medium when the pencil beam 31 penetrates the human body 32. S(E, 0) is the stopping power of the beam having incident energy E at the surface of the human body.

Figure 13:
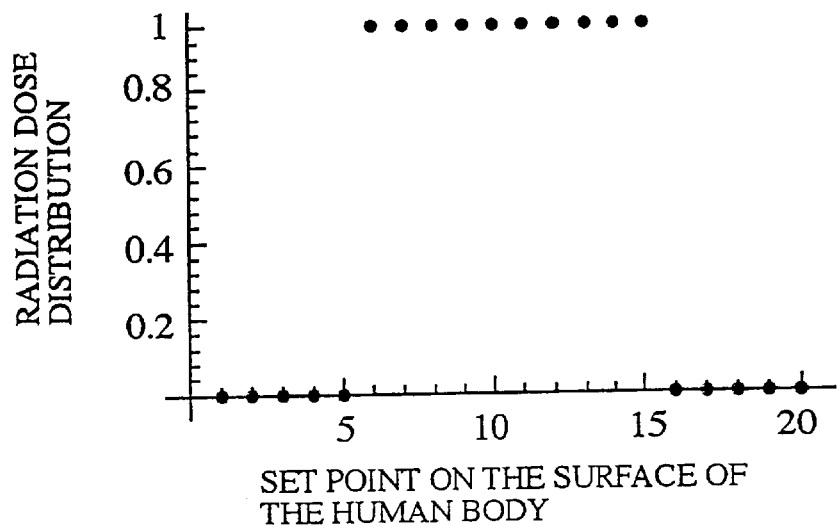
FIG. 13 is a graph showing the relation between radiation dose distribution and set point on the surface of the human body.

In Expression (6), S(E, 0)=1 for digitization. Suppose that a determinantal equation is expressed by U=AQ, where U is a dose distribution vector, Q is a pencil beam intensity vector, and A is system matrix. The component of the system matrix A is a Gaussian distribution function of Expression (6). Suppose, for example, that the pencil beam 31 is moved laterally in 100 steps to scan the human body 32 for irradiation, and desired dose distribution vectors V are set at twenty points on the surface of the human body as shown in FIG. 13.

The energy source density in the flow chart shown in FIG. 2 in this embodiment may be proton beam intensity. Since proton beam intensity is always not negative (0 or positive), $q_{min}=0$ and $q_{max}=1$ in step ST1 of FIG. 2. In steps ST2 to ST7, pattern coincidence degree, i.e., the degree of coincidence of the dose distribution U calculated by using Expression (6) with the desired dose distribution V, is evaluated. The third embodiment is the same in other respects as other embodiments.

Figure 14:
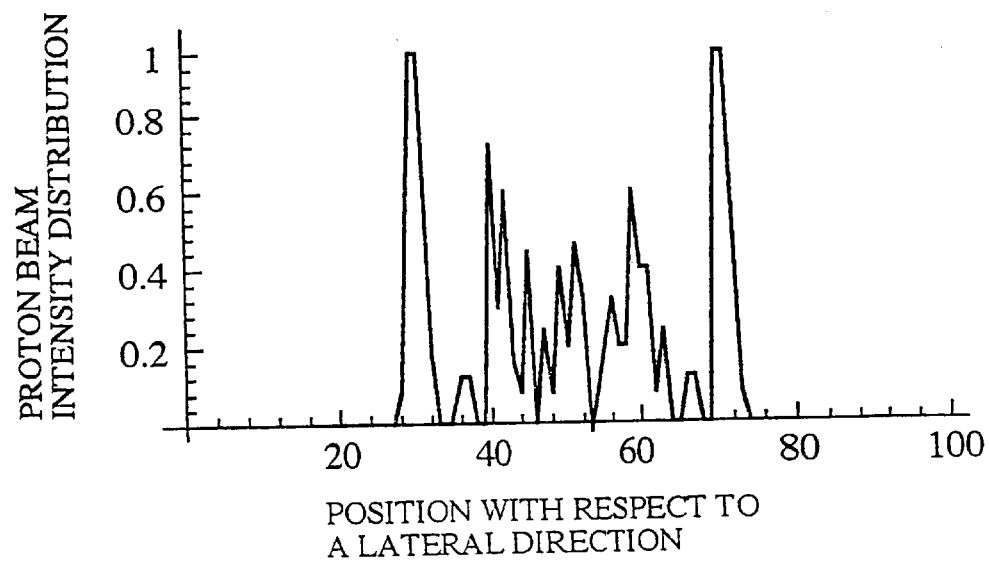
FIG. 14 is a graph showing the relation between electron beam intensity distribution and position with respect to a lateral direction.
Figure 15:
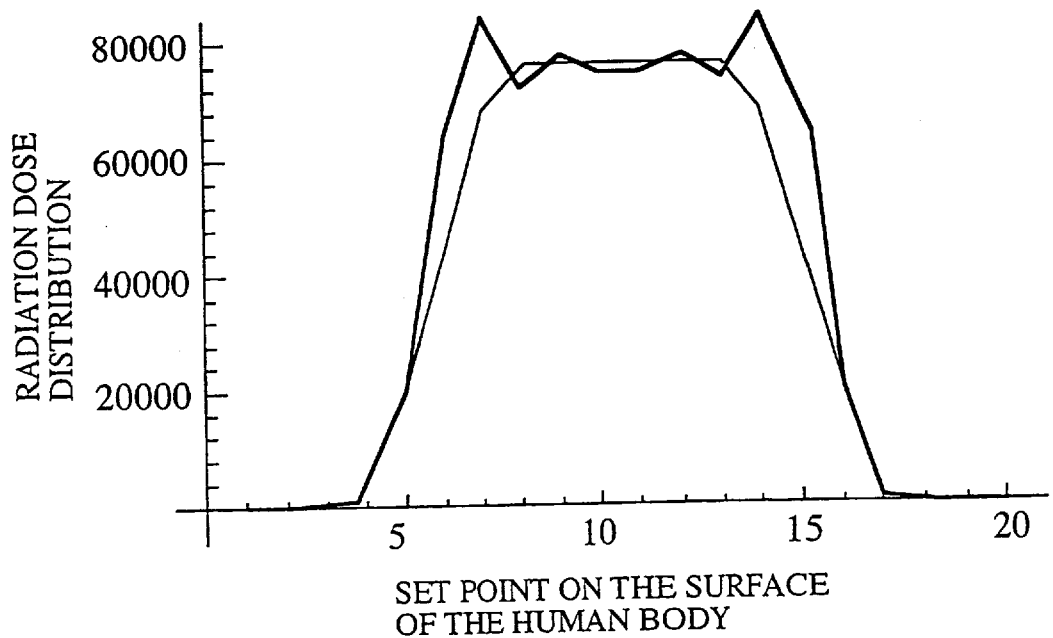
FIG. 15 is a graph showing the relation between radiation dose distribution and set position on the surface of the human body.

FIG. 14 is a graph showing the distribution of proton beam intensity with respect to the lateral direction determined by the third embodiment. In FIG. 15, a radiation dose distribution on the surface of the human body, namely, radiation doses at set points on the surface of the human body, is indicated by a distribution curve indicated by a thick continuous line. The distribution indicated by the thick line in FIG. 15 is close to the desired distribution shown in FIG. 12. In FIG. 15, a curve indicated by a thin continuous line represents a radiation dose distribution when a proton beam having a uniform intensity is used for irradiation. Although the proton beam intensity distribution shown in FIG. 14 is obtained, actual radiation dose is proportional to the product of proton beam intensity and the duration of irradiation. Therefore, the pattern shown in FIG. 14 may be regarded as a pattern of irradiation time for which the human body is irradiated with a proton beam of a fixed intensity.

Generally, it is desirable in proton therapy that the dose distribution has a sharp falling characteristic. It was found that the proton beam intensity distribution determined by the third embodiment has a sharper falling characteristic.

Although the energy source distribution in the objective system is the charge distribution or the proton beam intensity distribution in the foregoing embodiments, a particle beam (carbon or the like) other than the proton beam may be used.

An energy source distribution formed by the energy source in the system (current density distribution, magnetization distribution, heat source distribution, sound source distribution, voltage source distribution, electromagnetic field source distribution, light source distribution, load distribution, radio wave source distribution or radiation source distribution) can be determined by the method of the present invention so that a desired energy distribution (electric field distribution, magnetic field distribution, magnetic flux density distribution, stress distribution, displacement distribution, temperature distribution, heat flow velocity distribution, sound pressure distribution or radiation intensity distribution) can be formed.

Although the foregoing embodiments have been described in terms of the methods of determining a linear or one-dimensional energy source distribution, naturally, the present invention is applicable for the determination of a two-dimensional or three-dimensional energy source distribution.

Fourth Embodiment

Figure 16:
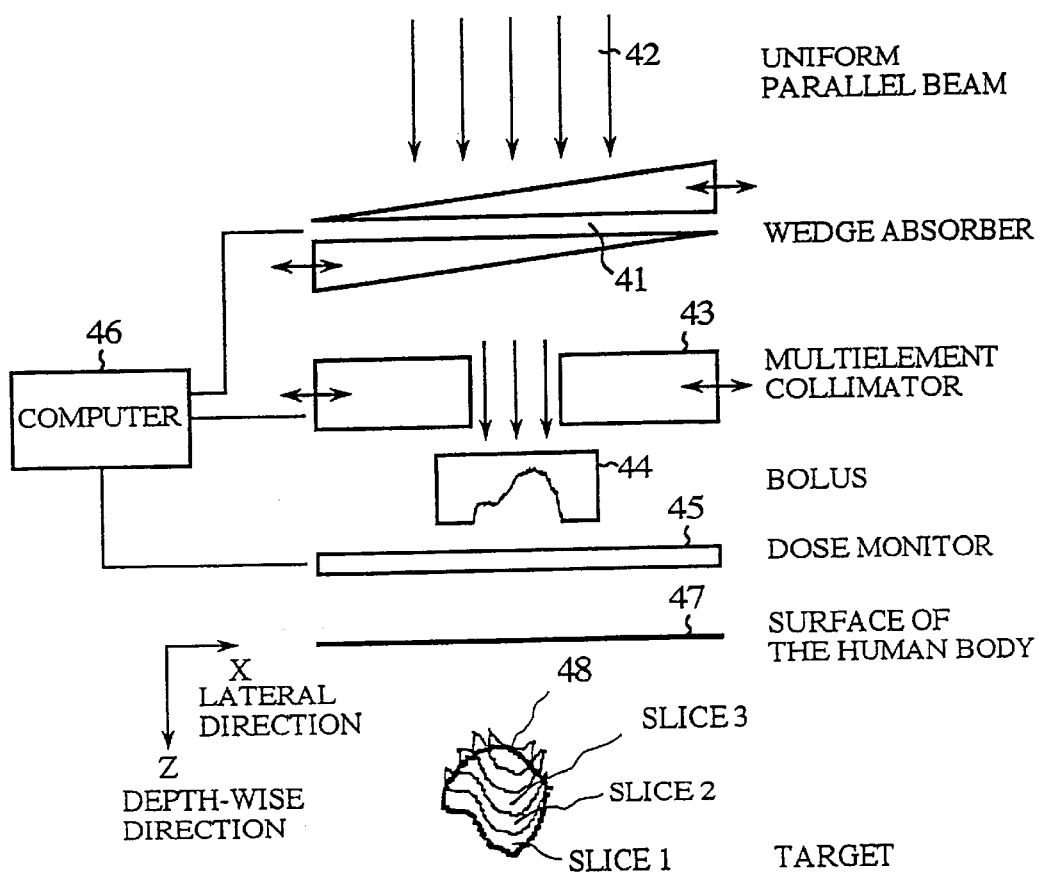
FIG. 16 is a block diagram of a proton therapeutic apparatus for carrying out an energy distribution forming method in a fourth embodiment according to the present invention.

FIG. 16 is a diagrammatic view of assistance in explaining an energy distribution forming method according to the present invention, showing a therapeutic apparatus to irradiate a target, such as a tumor in the human body, with a proton beam for therapy in a modification of a conventional proton therapeutic apparatus mentioned in "Medical Physics", Vol. 10, p. 344 (1983).

Referring to FIG. 16, there are shown s wedge absorber 41 on which a proton beam 42 of parallel proton rays falls, a multielement collimator 43 having elements moved in the directions of arrows to define a passage for the proton beam 42, a bolus for changing the energy of the proton beam, a dose monitor 45 for measuring radiation dose, a computer 46 which receives a measured value from the dose monitor 45, the surface 47 of the human body, a target 48, such as a tumor in the human body.

The operation will be described hereinafter.

The proton beam 42 of uniform, parallel rays falls from above on the wedge absorber 41, and the wedge absorber 41 reduces the energy of the proton beam 42. The elements of the multielement collimator 43 are moved according to the width of the tumor, and the bolus 44 adjusts the energy distribution in the proton beam 42. The wedge absorber 41 and the bolus 44 are made of a material having a proton attenuating characteristic similar to that of the human body, such as an acrylic resin.

The dose monitor 45 measures the dose of the proton beam, and gives a signal representing the measured dose to the computer 46 to control the timing of moving the wedge absorber 41 and the multielement collimator 43. The target is divided into virtual slices 1, 2, 3, . . . from the deepest portion upward, and the slices are irradiated sequentially to form dose distributions for the slices. The dose monitor 45 measures the dose in each slice and the pattern of the measured dose is controlled so as to coincide with a predetermined pattern. The dose is proportional to the integral of radiation intensity with respect to time. If a cyclotron is employed as an accelerator for producing the proton beam, it is usual to determine different irradiation times respectively for the slices to control the dose because the beam intensity (radiation intensity) is constant. If a synchrotron is employed as an accelerator for producing the proton beam, it is usual to control the dose on the basis of measured dose measured by the dose monitor because the beam intensity varies with time. When irradiating the human body with the proton beam 42, an irradiation dose distribution (energy source distribution) in the proton beam 42 is determined so that a desired radiation dose distribution (energy distribution) is formed in the human body.

Figure 17:
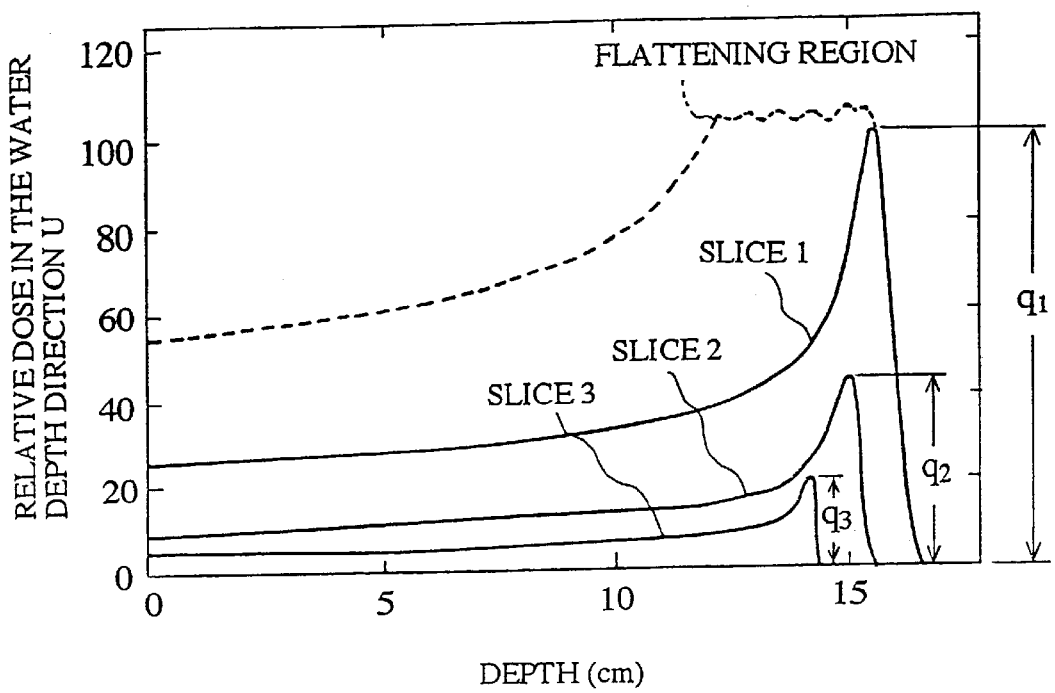
FIG. 17 is a graph showing the variation of internal dose with depth.

Generally, a dose distribution with respect to depth in the human body is expressed by FIG. 17, which was produced by modifying a drawing included in the aforesaid paper for better understanding. In FIG. 17, $q_1$, $q_2$ and $q_3$ are doses (energy source distributions) for the slices 1, 2 and 3. The graph of FIG. 17 is based on data obtained through experiments using a water model substantially equivalent to the human body. In FIG. 17, a curve indicated by a dotted line represents a dose distribution in the human body optimized by the conventional method, in which the flatness of a flattening region is unsatisfactory.

Figure 18:
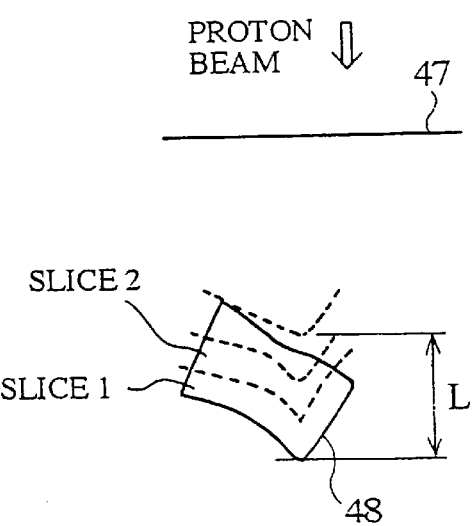
FIG. 18 is a diagram of assistance in explaining a method of irradiation with protons.

FIG. 18 illustrates an irradiating method in further detail. The number of slices conforming to the shape of a back portion of a target 48, such as a tumor, is obtained by dividing the representative length L of the target 48 by the thickness of each slice. For example, the number of slices is three if L=6 mm and the thickness of each slice is 2 mm.

Figure 19:
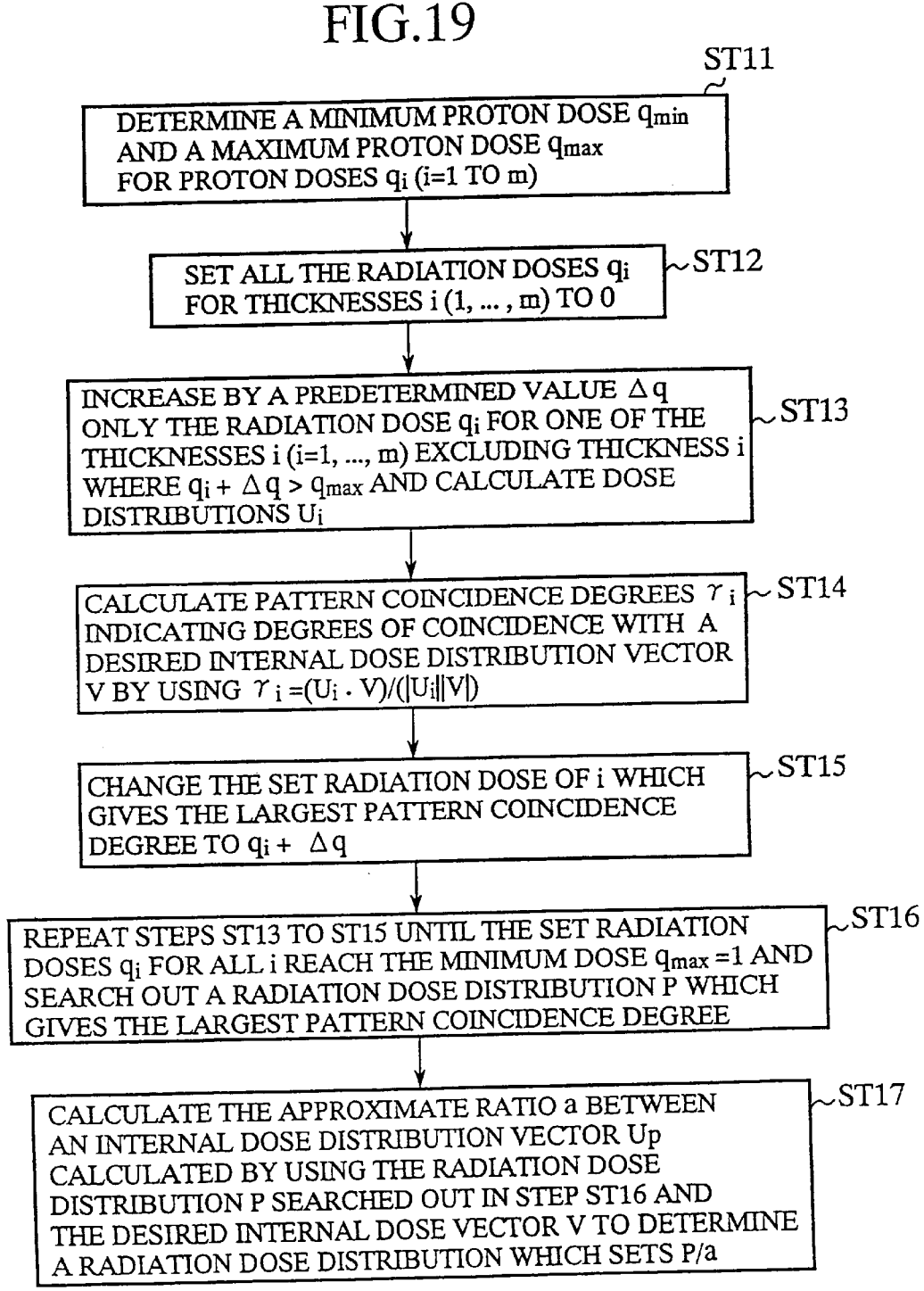
FIG. 19 is a flow chart of a process of determining a proton dose distribution.

FIG. 19 is a flow chart showing a procedure for determining the radiation dose distribution (energy source distribution) of the proton beam 42. The flow chart shown in FIG. 19 is similar to that shown in FIG. 2, except that the flow chart shown in FIG. 19 is a flow chart showing steps of determining the radiation dose distribution of the proton beam 42 which gives a desired internal dose distribution.

FIG. 20 illustrates a process of determining the radiation dose of the proton beam for the thickness of the wedge absorber 41. In FIG. 19, i=1 to m correspond to thickness of the wedge absorber 41, respectively. The thickness of the wedge absorber 41 is increased in a step of 2 mm. Therefore, i=1 corresponds to a thickness of 2 mm of the wedge absorber 41, and i=25 corresponds to a thickness of 50 mm of the wedge absorber 41. Others are the same as those shown in FIG. 5.

Figure 21:
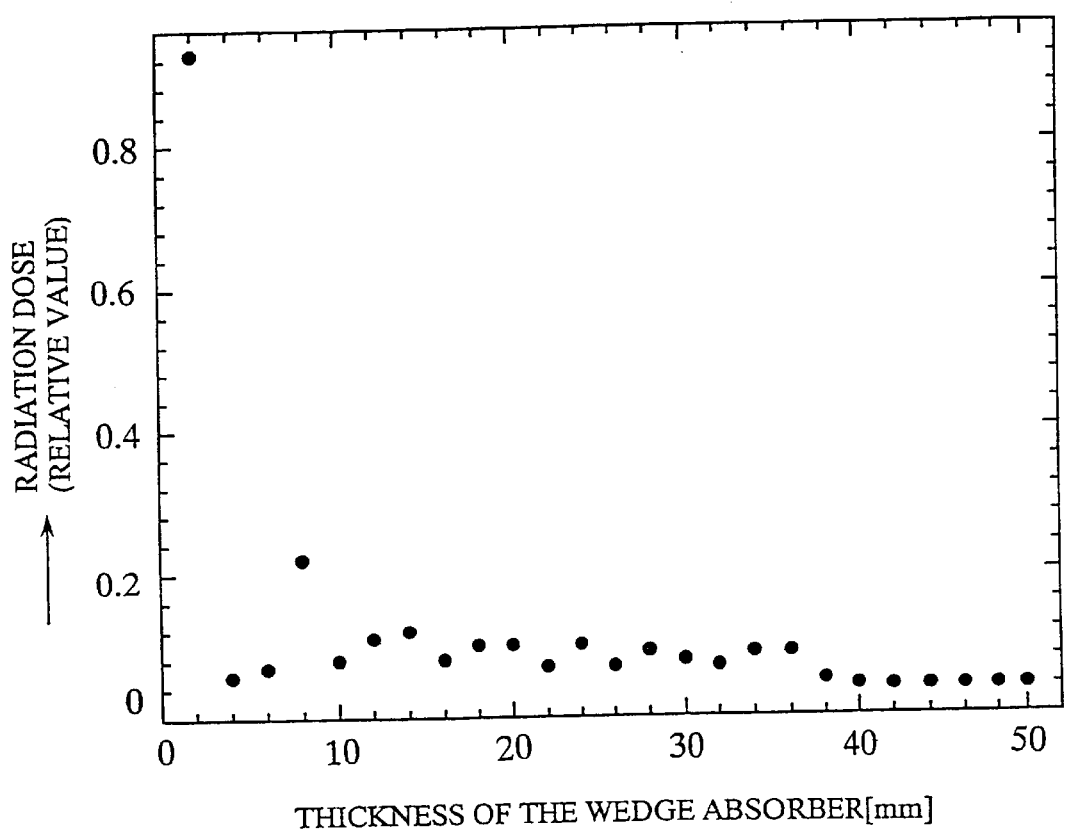
FIG. 21 is a graph showing the distribution of proton dose for the thickness of a wedge absorber.

FIG. 21 shows a radiation dose distribution for the thickness of the wedge absorber 41 calculated by an algorithm illustrated in FIGS. 19 and 20. FIG. 21 shows a solution which gives a maximum pattern coincidence degree corresponding to the radiation dose distribution P in step ST16 of FIG. 19.

Figure 22:
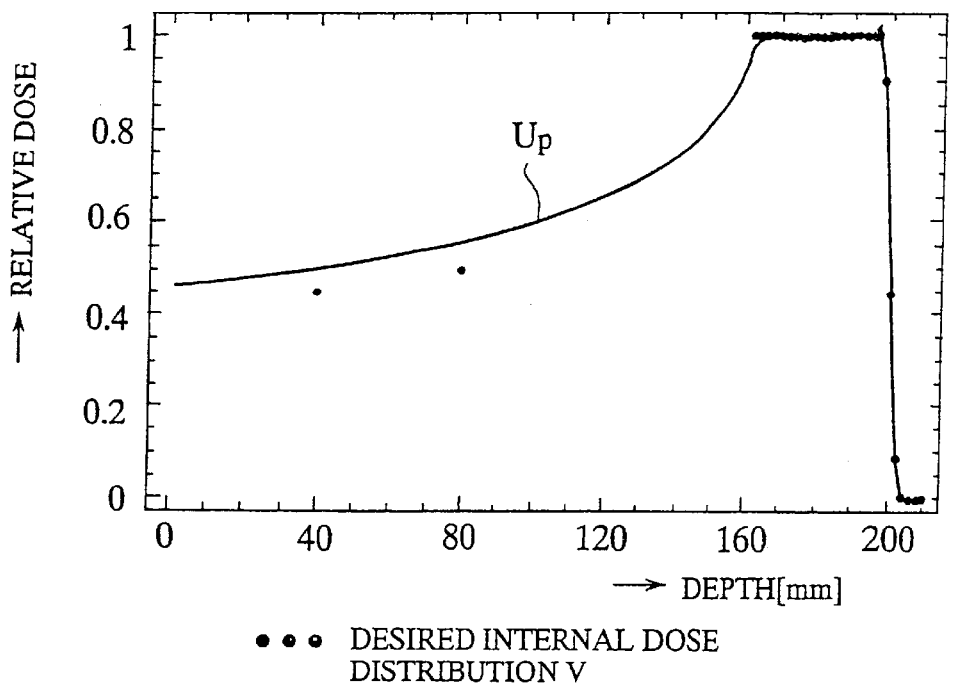
FIG. 22 is a graph showing the relation between a desired internal dose distribution and calculated internal dose distribution.

FIG. 22 shows a desired internal dose distribution V, and an internal dose distribution $U_P$ when the human body is irradiated in a radiation dose distribution determined by calculation according to the present invention, in which depth (depth in water simulating the human body) is measured on the horizontal axis. It is known from FIG. 22 that a desired internal dose distribution is formed.

Figure 23:
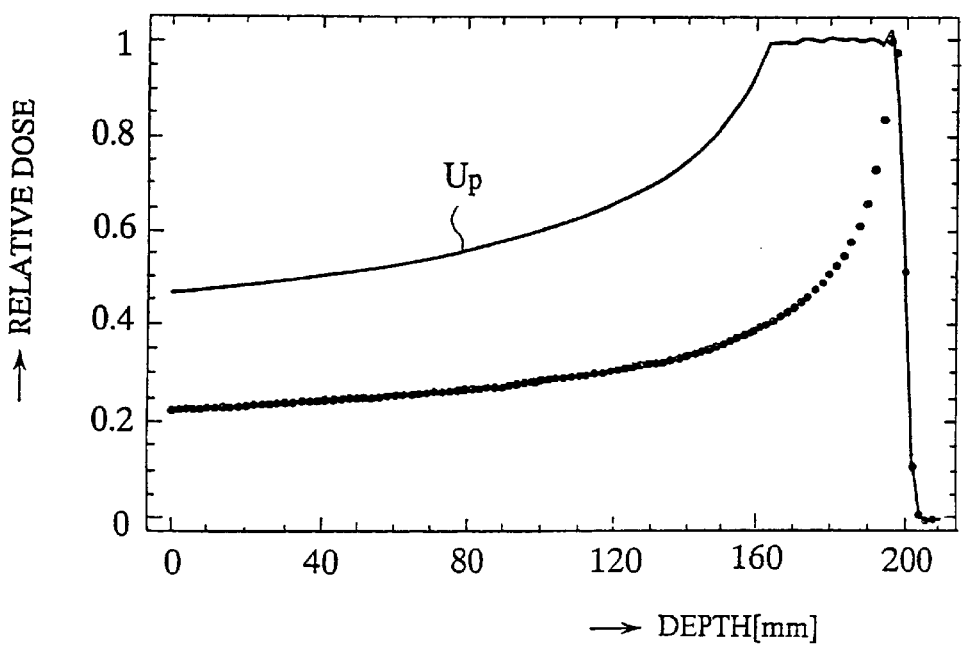
FIG. 23 is a graph showing, in combination, a calculated internal dose distribution and an internal dose distribution to which a monoenergetic proton beam is given.

FIG. 23 shows, in combination, an internal dose distribution $U_P$ formed when the human body is irradiated in a radiation dose distribution determined by calculation according to the present invention, and an internal dose distribution formed by a monoenergetic proton beam 42. It was found from the calculated radiation dose distribution that a dose attenuation characteristic in a portion deeper than the target region is the same as the attenuation characteristic of the monoenergetic proton beam 42, which is a necessary characteristic when an important organ which should not be irradiated with radioactive rays, such as the spinal cord, lies behind the tumor. The flatness of a predetermined range (range corresponding to the tumor) in the internal dose distribution formed by the present invention is about 2% or below, and dose attenuation characteristic in a portion behind the tumor is ideal. The result obtained by the present invention gives a theoretical limit because it is physically impossible to obtain an attenuation rate exceeding the attenuation characteristic of the monoenergetic proton beam 42.

Figure 24:
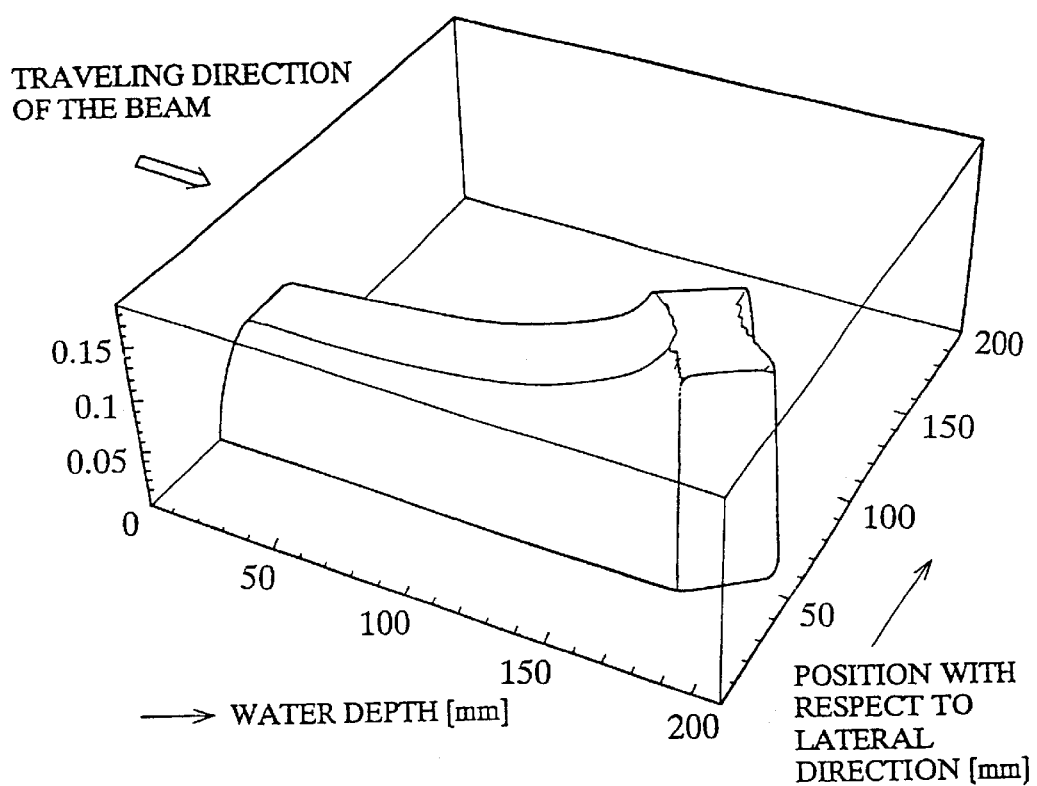
FIG. 24 is a diagrammatic view showing an internal dose distribution.

FIG. 24 shows an internal dose distribution formed when the tumor 18 shown in FIG. 18 lying deep in water is irradiated in the radiation dose distribution obtained by the present invention. In FIG. 16, the slices are irradiated sequentially, starting from the deepest slice 1, and the positions of the wedge absorber 41 and the multielement collimator 43 are adjusted for each slice. It is known that a uniform internal dose distribution is formed in the tumor.

Figure 25:
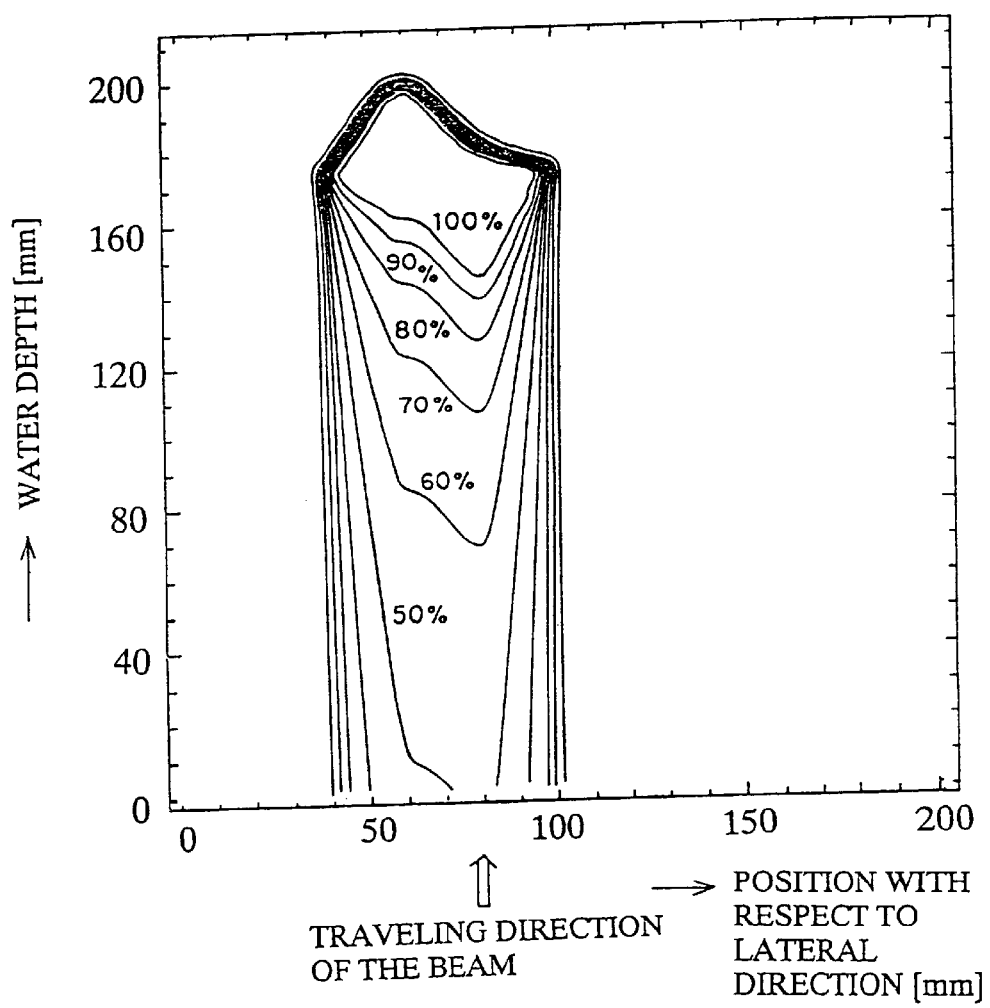
FIG. 25 is a graph showing an internal dose distribution indicated by contour lines.

FIG. 25 shows an internal radiation distribution by contour lines. It is known from FIG. 25 that the internal dose in the tumor is 100%, and the attenuation characteristic of the internal dose with respect to depth and lateral directions is very sharp and ideal.

Any suitable particle beam other than the proton beam, such as a helium beam, a carbon beam, a neon beam or any suitable particle beam, may be used instead of the proton beam.

Although the internal dose distribution formed in the water model shown in FIG. 16 is employed as the dose distribution $U_i$ with respect to depth shown in FIG. 18 in this embodiment to simplify explanation, it is desirable to use an internal dose distribution calculated with high accuracy on the basis of X-ray CT image data about the patient as the dose distribution $U_i$ with respect to depth of FIG. 18 for practical therapy. Monte Carlo method (Goiden, et al., "Radiation Research", Vol. 74, pp. 217–230 (1978)) and a method employing an infinite slab model (Russel, et al., Physics in Medicine and Biology, Vol. 40, pp. 1031–1043 (1995)) are known methods suitable for calculating an internal dose distribution with high accuracy on the basis of X-ray CT image data about the patient. The dose distribution $U_i$ with respect to depth calculated by those methods may be applied to the present invention.

Although only the dose distribution $U_i$ with respect to depth is varied in this embodiment, some therapeutic method (Kanai, et al., Nuclear Instruments and Method, Vol. 214, pp. 491–496 (1983)) divides a tumor in the human body into small voluminal elements and determines a radiation dose for each voluminal element.

In this case, a proton beam of about 6 mm in diameter is sent to the system shown in FIG. 16, and the proton beam of about 6 mm in diameter is moved for scanning in two directions, namely, an x-direction, and a y-direction perpendicular to the sheet, not shown, by a magnet. The energy of the proton beam to be projected on the human body is adjusted by the wedge absorber shown in FIG. 16 or an energy degrader having a function similar to the wedge absorber or by an accelerator which produces and accelerates a proton beam.

Consequently, the proton beam is capable of three-dimensional scanning. When the invention illustrated in FIG. 18 is applied to such a therapeutic apparatus, the internal dose can be adjusted for each small voluminal element and, therefore, a desired three-dimensional dose distribution can be formed.

Figure 26:
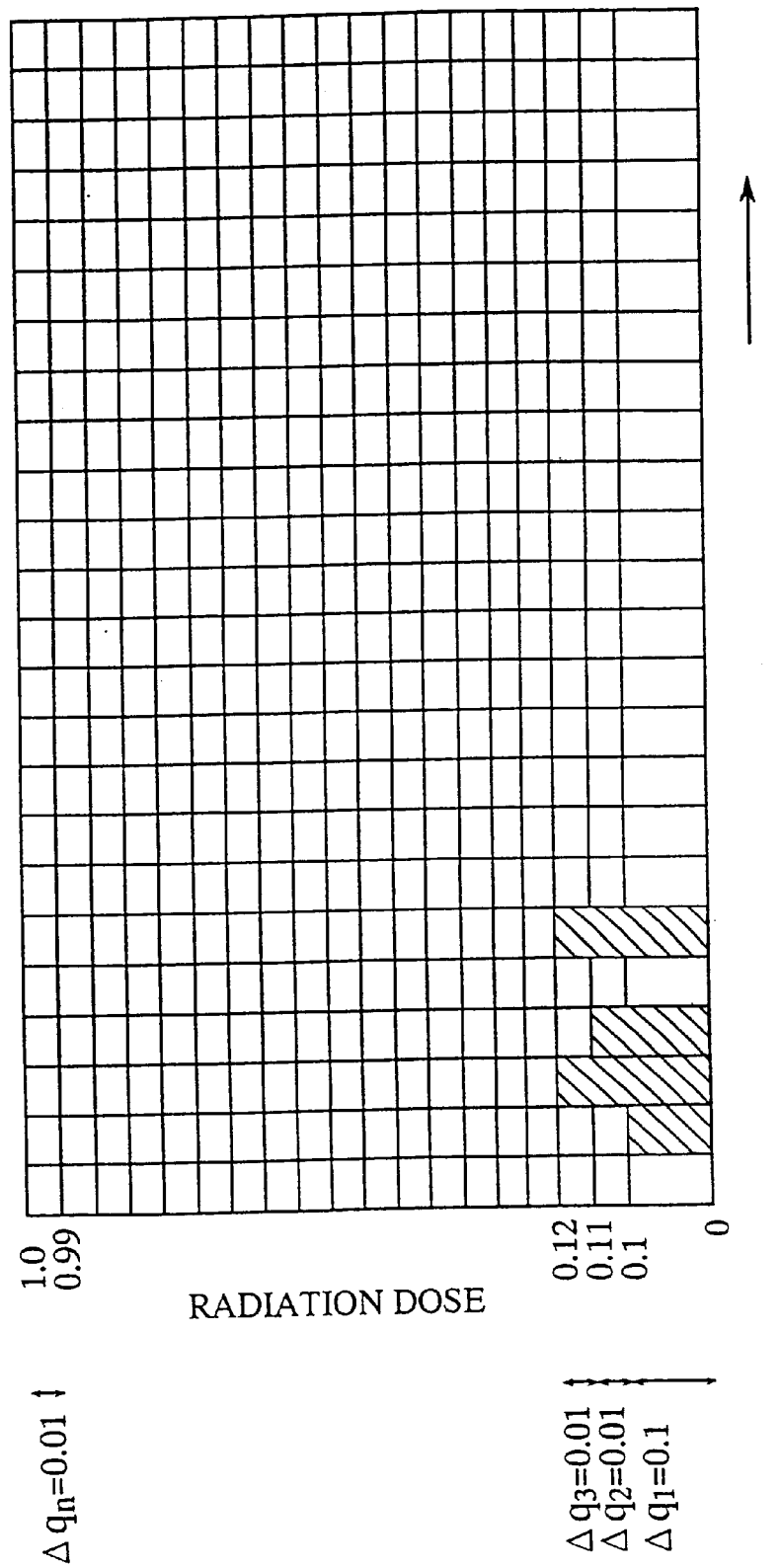
FIG. 26 is a diagram showing proton dose for the thickness of a wedge absorber.

Although the radiation dose of the proton beam is changed in a fixed step $\Delta q=1/50$ in FIG. 19, at least one of steps $\Delta q_1, \Delta q_2, \ldots$ and $\Delta q_n$ may be different from the rest of the steps as shown in FIG. 26. If, $$\sum_{j=1}^{n} \Delta q_j = q_{max} - q_{min}$$

steps can be expressed, q may be optionally determined, which is effective when a minimum set radiation dose cannot be a small value due to restrictions on the apparatus.

In FIG. 26, the minimum set radiation dose is 0.1, and the radiation doses are increased sequentially at a step of 0.01 up to a maximum radiation dose of 1.0. When the radiation dose is thus determined, substantially optimum dose control can be achieved even if the radiation dose cannot be set to a value of 0.1 or below due to restrictions on the apparatus; that is, the step q can be optionally determined in a range defined by:

$$\sum_{j=1}^{n} \Delta q_j = q_{max} - q_{min}$$

In FIG. 26, q=1 and q=0.

Industrial Applicability

As is apparent from the foregoing description, since the energy distribution forming method of the present invention is capable of varying the intensity of energy distribution, the energy distribution method of the present invention is able to irradiate a target, such as a tumor in the human body, for therapy by an energy distribution without irradiating an important organ lying behind the tumor.

What is claimed is:

1. An energy distribution forming method comprising:
   a first step of determining a minimum energy source density $q_{min}$ and a maximum energy source density $q_{max}$ for a desired electric field distribution;
   a second step of setting the minimum energy source density $q_{min}$ at m energy source density setting positions $x_i$ (i=1, ..., m);
   a third step of increasing by a predetermined value $\Delta q$ an energy source density $q_i$ of the energy source density setting positions $x_i$ (i=1 to m) excluding the energy source density setting positions $x_i$ where $q_i=\Delta q>q_{max}$, and calculating energy distribution vectors $U_i$, where $U_i=AQ_i$;
   a fourth step of calculating pattern coincidence degrees $\gamma_i$ from the calculated energy distribution vectors $U_i$ and a desired energy distribution vector V, where $\gamma_i=\cos\theta_i= U_i*V/(|U_i||V|)$:
   a fifth step of changing the energy source density at the position $x_i$ which gives the largest pattern coincidence degree to $q_i+\Delta q$;
   a sixth step of repeating the third step to the fifth step until the energy source densities at all the positions $x_i$ reach the maximum energy source density $q_{max}$ and searching out an energy source density distribution P which gives the largest pattern coincidence degree; and
   a seventh step of calculating the ratio a between an energy distribution vector $U_P$, calculated by using the energy source density distribution P searched out in the sixth step, and the desired energy distribution vector V to obtain an optimum energy source density distribution P/a.

2. The energy distribution forming method according to claim 1, wherein one of an electric charge density distribution, a particle beam intensity distribution, a current density distribution, a voltage source distribution, an electromagnetic field source distribution, a radiation source distribution, a heat source distribution, a light source distribution, a load distribution, a sound source distribution and a magnetization distribution is selected as an energy source distribution.

3. The energy distribution forming method according to claim 1, wherein one of an electric field distribution, a particle dose distribution, a potential distribution, an electromagnetic field distribution, a stress distribution, a displacement distribution, a temperature distribution, a flow velocity distribution, a sound pressure distribution and a radiation intensity distribution is selected as an energy distribution.

4. The energy distribution forming method according to claim 3, wherein a proton dose distribution is selected as a particle dose distribution, and a proton beam intensity distribution is selected as a particle beam intensity distribution.

5. The energy distribution forming method according to claim 1, wherein the cosines of angles between the calculated energy distribution vectors $U_i$ and the desired energy distribution vector V are used as pattern coincidence degrees.

6. The energy distribution forming method according to claim 1, wherein the sines of angles between calculated energy distribution vectors $U_i$ and the desired energy distribution vector V are used as pattern coincidence degrees.

7. The energy distribution forming method according to claim 1, wherein a particle dose distribution is selected as an energy source distribution, and an internal particle dose distribution is selected as an energy distribution.

8. The energy distribution forming method according to claim 1, wherein a proton beam is selected as a particle beam.

9. The energy distribution forming method according to claim 1, wherein the value of $\Delta q$ for i=1 to m is determined selectively so that $\Delta q_j$ (j=1, ..., n) meet an expression:

$$\sum_{j=1}^{n} \Delta q_j = q_{max} - q_{min}.$$

10. An energy distribution forming method comprising:
- a first step of determining a minimum energy source density $q_{min}$ and a maximum energy source density $q_{max}$ for a desired electric field distribution;
- a second step of setting the minimum energy source density $q_{min}$ at m energy source density setting positions $x_i$ (i=1, ..., m);
- a third step of decreasing by a predetermined value q an energy source densities $q_i$ at the positions $x_i$ (i=1, ..., m) excluding the positions $x_i$ where $q_i=\Delta q<q_{min}$, and calculating energy distribution vectors $U_i$, where $U_i=AQ_i$;
- a fourth step of calculating pattern coincidence degrees $\gamma_i$ from the calculated energy distribution vectors $U_i$ and a desired energy distribution vector V, where $\gamma_i=\cos\theta_i= U_i*V/(|U_i||V|)$;
- a fifth step of changing the energy source density at the position $x_i$ which gives the largest pattern coincidence degree to $q_i-\Delta q$;
- a sixth step of repeating the third step to the fifth step until the energy source densities at all the positions $x_i$ reach the minimum energy source density $q_{min}$ and searching out an energy source density distribution P which gives the largest pattern coincidence degree; and
- a seventh step of calculating the ratio a between an energy distribution vector $U_P$, calculated by using the energy source density distribution P searched out in the sixth step, and the desired energy distribution vector V to obtain an optimum energy source density distribution P/a.

* * * * *